United States Patent [19]

Whalley

[11] 4,121,592
[45] Oct. 24, 1978

[54] APPARATUS FOR HEATING TISSUE

[75] Inventor: Wilfrid B. Whalley, Palo Alto, Calif.

[73] Assignee: Critical Systems, Inc., Palo Alto, Calif.

[21] Appl. No.: 705,524

[22] Filed: Jul. 20, 1976

Related U.S. Application Data

[63] Continuation-in-part of Ser. No. 643,515, Dec. 22, 1975, abandoned, which is a continuation-in-part of Ser. No. 601,257, Aug. 4, 1975, abandoned.

[51] Int. Cl.$^2$ ............................................. A61N 1/40
[52] U.S. Cl. ................................... 128/413; 128/399; 128/404; 128/422; 331/183
[58] Field of Search ............... 128/413, 404, 405, 417, 128/419 R, 420, 422, 399, 1.3–1.5, 2.1 P; 331/183

[56] References Cited

U.S. PATENT DOCUMENTS

| 2,223,447 | 12/1940 | Hathaway | 128/413 |
|---|---|---|---|
| 3,245,408 | 4/1966 | Gonser | 128/422 |
| 3,668,556 | 6/1971 | Harbeson | 331/183 |
| 3,800,802 | 4/1974 | Berry et al. | 128/422 |
| 3,886,932 | 6/1975 | Suessmilch | 128/2.1 P |
| 3,991,770 | 11/1976 | LeVeen | 128/413 |
| 4,016,886 | 4/1977 | Doss et al. | 128/422 |
| 4,032,860 | 6/1977 | LeVeen | 128/422 X |

FOREIGN PATENT DOCUMENTS

| 2,356,183 | 10/1974 | Fed. Rep. of Germany | 128/404 |
|---|---|---|---|
| 1,056,290 | 4/1959 | Fed. Rep. of Germany | 128/422 |
| 1,284,528 | 12/1968 | Fed. Rep. of Germany | 128/1.5 |
| 862,014 | 2/1941 | France | 128/420 |

OTHER PUBLICATIONS

Geyser, "Diathermia . . . Treatment of Cancer", Fischer's Magazine, Jan. 12, 1925.
Schereschewsky, "The Action of Currents . . . Tissue Cells", U.S. Public Health Reports, vol. 43, Apr. 1928, No. 16, pp. 927–939.
Warren, "Prelim. Study . . . Tumor Cases", Am. J. of Roent. and Radium Therapy, vol. 33, No. 1, 1935, pp. 75–87.
Goldenberg et al., "Direct . . . Action of Local Hyperthemic", Zeitschrift Fur Natur., 26:Apr. 1971, pp. 359–360.

Primary Examiner—Lee S. Cohen
Attorney, Agent, or Firm—Fitch, Even, Tabin & Luedeka

[57] ABSTRACT

Apparatus is described for heating tissue and which is particularly useful for treating tumors in humans and animals. An electric field is produced across two electrodes or one electrode and ground, and is passed through both the tumor and the surrounding tissue. The polarity of the electric field is varied at radio frequency. The power of the electric field is efficiently coupled into the tissue being heated. Direct current inverse feedback circuitry enables close control of tissue temperatures.

10 Claims, 3 Drawing Figures

APPARATUS FOR HEATING TISSUE

This application is a continuation-in-part of application Ser. No. 643,515 filed Dec. 22, 1975, now abandoned, which was a continuation-in-part of Application Ser. No. 601,257 filed Aug. 4, 1975 now abandoned.

This invention relates generally to the treatment of tissue. More particularly, the invention relates to apparatus for heating tumors in humans and animals to a higher temperature than the surrounding tissue.

One of the known characteristics of certain types of tumors is that the blood circulation rate therein is significantly less than that in normal or healthy tissue. (See Encyclopedia Britannica pa. 769 — "Cancer"). For example, certain types of tumors have a blood circulation rate which is as low as one-half that of normal surrounding healthy tissue. This fact is considered to be the cause of a contributory factor in the selective heat sensitivity of many types of malignant tumors.

The treatment of tumors by selective heating has been reported in the literature. (See Surgery, Gynecology and Obstetrics, Volume 140, No. 3, March, 1975, *Results of Hyperthermic Perfusion for Melanoma of the Extremities*, Stehlin, Jr., Giovanella, Ipolyi, Muenz, and Anderson.). Techniques for selective heating have included hyperthermic perfusion, diathermy, and the induction of fever.

For various reasons, however, success in the treatment of tumors and in particular malignant tumors has been limited. For example, in the case of hyperthermic perfusion, some undesirable damage to healthy tissue has often resulted and the technique is only suitable for the treatment of tumors in limbs. Although a form of diathermy has been used successfully to treat tumors near the skin surface, specifically the use of a probe or stylus inside the rectum to produce a small area of electrically induced heating in the treatment of rectal tumors, tumors any substantial distance below the surface of the skin have typically been untreatable. Finally, although fever has caused remission in some cases, prolonged induction of fever may have considerable undesirable side effects.

Experiments conducted at the Royal Victoria Infirmary, Newcastle-Upon-Tyne, England, during the late 1930's have been reported in the American Journal of Cancer, Vol. 28, November, 1936, pp. 603–620; Vol. 30, June, 1937, pp. 341–354; and Vol. 38, 1940, pp. 533–550. These experiments succeeded in destroying tumors in rats and mice through the use of radio frequency electric fields. Treatment, however was limited for the most part to relatively small volumes of tissue, and success was generally limited to surface tumors. In many cases the skin was damaged as well as the tumor. Moreover, very high field densities were employed in the aforementioned experiments resulting in little if any selective heating between the tumor and the surrounding tissue. Finally, the frequencies used in the experiments and the type of apparatus employed resulted in poor coupling of the power of the apparatus into the tissue being heated and poor control over power levels.

The basic elements described above are disclosed by the prior art. Thus Wappler U.S. Pat. No. 1,480,353, Jan. 8, 1924, shows the use of a pair of padded capacitive plates attached to handles and used to apply high frequency currents to human tissue for medical or therapeutic purposes. Carpenter et al, "*Production of Fever in Man by Short Wave Radio Waves*", Science, May 2, 1930, LXXI, 450-2, discuss the production of artificial fever in man by short radio waves to whole body temperature of 104° F. for therapeutic purposes. A frequency of $10^4$ mHz was used with capacitive plates 28 × 18 inches covered by rubber insulation. The vacuum tube oscillator had an output of 500 watts at 3,000 volts. Commenting on the Carpenter et al work in 1933, Schereschewsky, J. W., Radiology 20:246, 1933, noted the difference between electrostatic heating and conventional diathermy where there was an actual flow of current between the electrodes. Schereschewsky suggested the use of high frequency condenser fields to raise the temperature of deep-seated organs to a considerable degree without, at the same time, overheating the subcutaneous tissue.

Although the production of a high frequency electric field is relatively simple from an engineering point of view, the above reports suggest considerable lack of sophistication in the apparatus used. The mere connection of a pair of capacitive plates to the combination of an oscillator and amplifier does not provide the degree of control over heating rates and temperatures needed for a truly effective tumor treatment.

It is an object of the present invention to provide an improved apparatus for the treatment of tumors.

Another object of the invention is to provide an improved apparatus for heating tumors without adverse effects to surrounding tissue.

A further object of the invention is to provide apparatus for heating tumors to a higher temperature than the surrounding tissue.

Other objects of the invention will become apparent to those skilled in the art from the following description, taken in connection with the accompanying drawings wherein.

Figure 1:
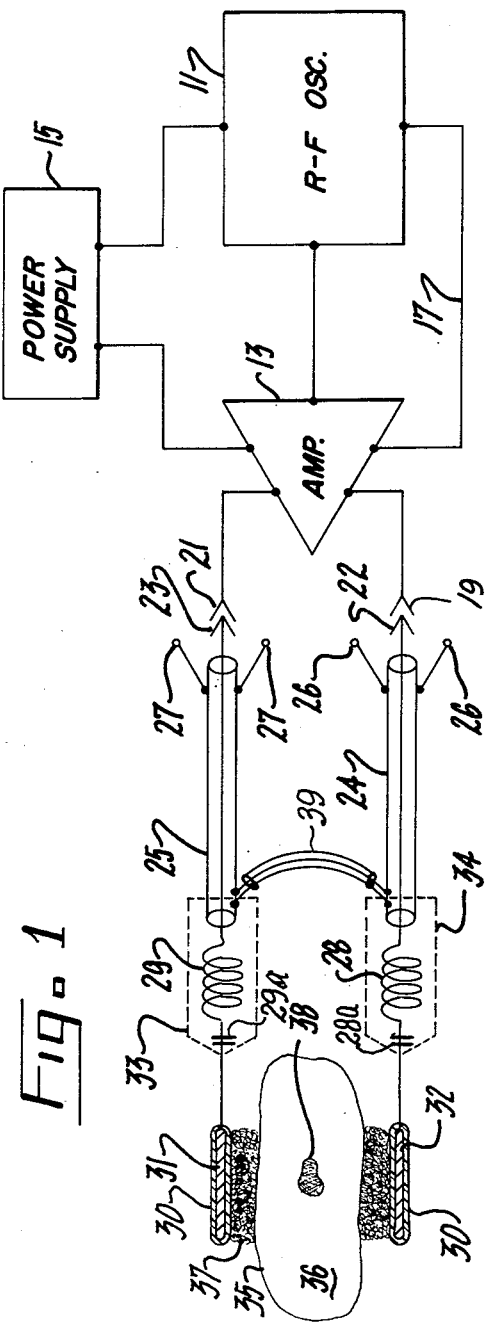
FIG. 1 is a schematic block diagram of apparatus constructed in accordance with the invention.

Very generally, the apparatus of the invention comprises radio frequency oscillator means and amplifier means coupled to the output of the radio frequency oscillator means for producing an amplified radio frequency output signal. Electrode means are coupled to the amplifier means and include at least one capacitive electrode having a configuration adapted to pass an electric field through both the tumor and the surrounding tissue. Means are provided for controlling the power of the amplifier means to avoid heating the surrounding tissue beyond a preselected temperature level while allowing the tumor to heat beyond the preselected temperature level. The controlling means include direct current inverse feedback means connected from the amplifier means to the oscillator means for stabilizing the output current.

The higher sensitivity of malignant tumors to heat has been taken advantage of in a number of techniques as previously mentioned. One such technique is the use of so-called diathermy in which magnetic fields produced by suitable coils of the type used for physical therapy have been used to attempt to heat malignant tumors. The results of such attempts, however, have produced very limited, if any, success. Attempts to heat tumors typically resulted in damage to the skin, without successful results in destroying the tumor.

The present invention results from a recognition that diathermy techniques for the treatment of malignant tumors did not succeed because of skin effects inherent with live tissue in electromagnetic fields, and also the very limited volume of the effective electromagnetic field (that is an effective field only in close proximity to the coil itself). More particularly, any tissue which has a resistivity of approximately 50 ohms per cubic centimeter, when placed in an electromagnetic field, will have eddy currents generated close to its surface. These eddy currents operate in the same manner as the eddy currents in a conductive shield surrounding a vacuum tube or the like, preventing penetration of the electromagnetic field below the region in which the eddy current are generated. Typically in the case of the human body such eddy currents are generated in a more highly conductive subcutaneous layer lying slightly beneath the surface of the skin. Eddy currents are usually not generated in the skin surface because the surface cells of the skin are dead and of substantially less conductivity.

In accordance with the invention, the field utilized for treating the tumors is an electic field, sometimes referred to by those skilled in the art as an E-field or an electrostatic field. Unlike an electromagnetic field, the lines of force of an electric field are typically unclosed on each other and, when the field is formed between substantially parallel plates as in a capacitor, the lines of force typically run approximately parallel with each other between the plates. By passing such a field through a malignant tumor and the surrounding tissue approximately uniformly, and by varying such field at a radio frequency, heating of the tumor and the surrounding tissue will occur. Because the circulation rate and hence the cooling effect in the tumor is substantially lower than that in the healthy surrounding tissue, the tumor heats to a higher temperature. Some observations have indicated that the higher temperature of the tumor may also result in a further decrease in circulation within the tumor, and it is estimated that temperature increase within the tumor can be as much as 2 to 3 times as great as in the surrounding tissue. By selecting a predetermined upper temperature limit for the surrounding tissue and/or the body as a whole, for example 140° F. as measured orally, the power of the electric field may be regulated such that the surrounding tissue does not exceed the predetermined temperature but the temperature of the tumor being treated does exceed the predetermined temperature. Because the temperature of the tumor typically exceeds the predetermined temperature by a substantial magnitude, by maintaining this temperature differential for a sufficient period of time, the tumor may be killed.

Further, the treatment of tumors with a combination of heat and chemotherapy or heat and radiation has been extensively reported in the literature. (See Cancer Research, 30: 1623-1631, 1970, Effects of Elevated Temperatures and Drugs on the Viability of L1210 Leukemia Cells; or European J. Cancer, 8: 573-576, 1972, Investigations of II the Action of Combined Heat — Roentgen Treatment on a Transplanted Mouse Mammary Carcinoma). This invention may be used to heat tumors in conjunction with treatment by chemotherapy or Roentgen radiation in such a way as to enhance the effectiveness of these treatments.

As previously mentioned, electric fields have been used in the past in attempts to treat tumors. Such fields, however, have been utilized in such a way that the phenomenon of different circulation rates between tumors and healthy tissue has not taken advantage of. The present invention enables utilization of electric fields for the purpose of taking advantage of the aforementioned difference in circulation rates by efficiently coupling the electric field to the tissue being treated while at the same time providing the ability to effectively and closely control the power being applied to the tissue.

Referring now more particularly to FIG. 1, apparatus for performing the method of the invention is illustrated. The apparatus includes a radio frequency oscillator 11 of any suitable type for providing a radio frequency output. For reasons which are explained below, this frequency should be less than about 40 MHz and greater than about 2 MHz. The Federal Communications Commission in the U.S.A. has allocated 13.56 MHz or the second or third multiple thereof as the frequencies to be used in diathermy equipment, and 13.56 MHz is preferred over the higher multiples.

The output of the oscillator 11 is coupled to a radio frequency amplifier 13. Both the oscillator and the amplifier are powered by a suitable power supply 15, and a feedback circuit 17 is provided from the amplifier to the oscillator as a stabilizing device. The amplifier is provided with two outputs indicated at 19 and 21. One of the outputs may be used alone to establish an RF output between the attached electrode and ground as described below in connection with FIG. 3 or both the outputs 21 and 19 may be utilized together to provide an RF output therebetween.

As illustrated in FIG. 1, a radio frequency coaxial plug 23 is utilized to connect a coaxial cable 25 to the output 21 of the amplifier 13. Suitable ground connections 27 are provided to the sheath or shield of the cable 25 as is known in the art. The coaxial cable 25 is connected to a coil or choke 29 to connect the output from the terminal 21 of the amplifier 13 to a conductive plate 31. Similarly, a radio frequency coaxial plug 22 is utilized to connect a coaxial cable 24 to the output 19 of the amplifier 13. Suitable ground connections 26 are provided to the shield of the cable 24 as is known in the art. The coaxial cable 24 is connected to a coil or choke 28 to connect the output from the terminal 19 of the amplifier 13 to a conductive plate 32.

In addition, the sheaths of the cables 24 and 25 are interconnected by a flexible jumper cable 39, also coaxial. The cable 39 is connected by both central conductor and sheath to the sheaths of the cables 24 and 25 at the ends of the cables 24 and 25 just inside of the handles 33 and 34. The jumper lead 39 has the function of reducing the voltage drop between the open ends of the cable sheath, that is between the ends farthest from the power source. It also reduces the voltage drop between the power ground and the open ends of the sheath by providing a return path for the ground-side currents. The power coupling to the paddles or electrodes 31 and 32 is improved by a ratio of two to three times over the case where a jumper cable is not employed. The flexibility of the cable 39 allows freedom of positioning of the electrodes 31 and 32 while maintaining good coupling into the tissue as electrode sizes and corresponding spaces change.

The plates 31 and 32 are of a shape suitable for the purpose of applying an electric field of the desired configuration. Preferably, their diameter is about ten to twenty percent greater than the maximum dimension of the tumor in a plane perpendicular to the field. Insulation 30 may be provided over the entire surface of the plates 31 and 32 including the edges to prevent shorting of the plates to the tissue being treated. The thickness of the insulation 30 is shown in FIG. 1 exaggerated but is sufficiently thick so as to prevent direct conductive contact between the conductive plates and the skin. However, the thickness should not be so great as to inhibit coupling of the electric field to the tissue being treated. Accordingly, it is preferred that the insulation layer be a thin layer of low loss dielectric material such as polyurethane. The thickness of the plates 31 and the material thereof are selected to provide substantially uniform field density between their larger surfaces. Thus, a material having good electrical conductivity, such as copper or aluminum is used.

In a typical application, the plates 31 and 32 are circular discs, substantially flat, and are provided with insulating handles 33 and 34 to assist in manual placement of the plates 31 and 32. The coils or chokes 29 and 28 are contained within the handles 33 and 34, respectively, and are selected to have an inductance to couple the plates 31 and 32 to the driving amplifier and oscillator 13 and 11. More particularly, the sizes of the chokes 28 and 29 are selected such that the resulting inductive reactance provided in the circuit approximately balances and cancels out the capacitive reactance of the circuit provided by the plates, thereby ensuring that good coupling of the electric field into the tissue will result.

The insulation layer 30 on each of the electrodes is for the purpose of preventing low frequency transient voltage pulses from reaching the tissue being treated. When the radio frequency power source is turned on or off, frequencies are present in the circuitry, as may be shown by Fourier series analysis, which may extend down to d-c. The insulation in series with the electrode and the tissue has such an inherently low capacitance (less than 1000 pF) that it inhibits very low frequencies and d-c from reaching the tissue.

It should be noted, however, that the location of the capacitance for inhibiting low frequencies and d-c from reaching the tissue need not be physically located on the surface of the electrodes themselves. Another location, which has several advantages, is in the handles. To this end, high voltage highly stable capacitors 28a and 29a may be located in the handles 34 and 33, respectively. The capacitors 28a and 29a are, respectively, connected in series with the coils 28 and 29 in the handles. By choosing an inductance in the handles as determined by the coils 28 and 29 equal to the capacitance as before, only with the capacitance this time being determined by the capacitors 28a and 29a, significant advantages accrue. In other words, the capacitive reactance of the capacitor 28a or 29a is substantially equal to the inductive reactance of the coils with which it is in series (and 180° out of phase). The electrodes 31 and 32 may then be polished metal, rather than insulated, avoiding the possibility of the coated electrode developing scratches through which current could pass. A stable accurately known capacitance is provided in the handles which does not vary in capacitance as compared with variations in the capacitance of the coating on the electrodes as the coating varies in thickness with fabrication. Also, with very small electrodes, where the surface capacitance of the electrode coating is very small, the requirement for a large inductance is avoided, avoiding the corresponding very high voltage developed across both the coil and the electrode insulation.

The tissue into which the electric field is being coupled, is indicated substantially in cross section at 36 which may represent, for example, a portion of a human body. A tumor may be located at 38. Where surface irregularities exist, such as the undulations illustrated, coupling may be assisted by using a conductive deformable material 37, such as copper "wool", between the plates 31 and 32 and the undulating surfaces 35. Thus, irregularities such as those produced by ribs and other bony structures or by a protruding tumor are easily accommodated. A further improvement in coupling results if the skin surface is coated with a conductive paste, such as the jelly used for attaching the electrodes of an electrocardiogram machine.

Figure 3:
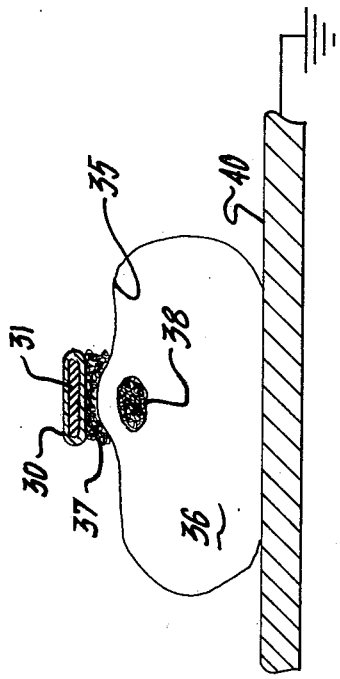
FIG. 3 is a cross sectional schematic view illustrating another manner in which the invention may be employed.

In applying the field, the plates or paddles 31 and 32 act as the plates of a capacitor, between which the tissue is placed. Each of the paddles may have RF voltage applied thereto, 180° out of phase, or one of the paddles may be grounded. Thus, for example, the paddle 31 may alternately become positive and negative with respect to ground, and the paddle 32 may become negative and positive, respectively; or the paddle 32 may instead remain at ground. Another possible configuration is to use only a single paddle and place the tissue on a grounded conductive plate, such as a metal examination table 40 tied electrically to the chassis of the apparatus. This is illustrated in FIG. 3. The configuration of FIG. 3 is typically preferred where the tumor is much closer to one surface than the other, as shown.

It is preferred that the conductive plates or paddles 31 and 32 be as close to the skin or tissue surface as possible to minimize the air gap between the plates and the surface. The copper wool or other deformable conductive material 37, as previously mentioned, takes up the irregularities and improves coupling from the electrodes into the tissue. A flexible electrode may be an alternative possibility or the use of a mesh of wires or a conductive coating on skin may also make it possible to couple the field into the tissue. The smaller the size of the region of coupling, the greater the impedance in the circuit, and this means more reactive power is wasted and therefore less useful power is applied to the tissue. However, the reactive impedance may be cancelled by using inductive coils such as coils 28 and 29 in FIG. 1. In addition, higher voltages are required with poorer coupling in order to carry the current, and the current density will also be correspondingly higher with a consequent higher risk of damage to the skin or the healthy tissue. Moreover, with higher current densities and higher voltage levels, control over the power being applied to the tissue is more difficult.

The shape of the conductor, as previously mentioned, may be circular, but other shapes are possible within the scope of the invention. The shape primarily depends upon the shape and location of the tumor being treated but in every case it is significant that the electric field be as uniform as possible and that the tumor be fully included within the uniform portion of the electric field. To this end, the electrodes or paddles may be held in place by any suitable means such as by hand, by an external mechanical structure, by adhesive tape, or by a conductive adhesive on the surface of the tissue.

As previously mentioned, the frequency at which the apparatus operates should be less than about 40 MHz and greater than about 2 MHz. At frequencies greater than about 40 MHz, the electrodes or paddles, and some other structural items, begin to act as antennae and radiate in all directions. Above 40 MHz, this radiation becomes significant and results in a significant wasting of power and therefore a substantially less efficient apparatus. Moreover, above about 40 MHz frequency, the surface of the tissue has a tendency to heat undesirably. This can be dangerous, especially to eye tissue. Other undesirable affects of operation at relatively high frequencies is that losses in a coaxial cable increase with increasing frequencies and that heat dissipation internally of the RF oscillator or amplifier may present a problem. Naturally, considerations of allocation of frequencies by government agencies is also a significant factor. Further difficulty with relatively higher frequencies include increased cost of manufacturing the apparatus, difficulty in controlling and measuring the actual RF current going to the tissue, and a wandering of the electric field at higher frequencies.

More significant, however, from a practical standpoint is the limitation that frequency places upon the length of coaxial cables which may be employed. The longer the coaxial cable length is relative to the wavelength at the frequency used, the more sensitive the circuit becomes to variables such as the resistive and capacitive loads and the electrode configuration. This is because any shunt capacitive load at the end of a coaxial cable substantially increases its "electrical" length. Thus, a substantial increase in control problems results where the coaxial cable length is long relative to the wavelength at the particular frequency selected.

As a practical matter, it has been determined that the total length of the coaxial cables, including the length inside of the apparatus itself, should not exceed about one-twentieth of the wavelength at the frequency being used. At the 13.56 MHz allocated for diathermy equipment, the wavelength is about 14.6 meters. Using the above criterion, a total coaxial cable length of about 73 centimeters or less is desirable. Since as much as 20 centimeters or more of coaxial cable may be utilized inside the apparatus itself, the length of the coaxial cable leads 24 and 25 at this frequency should be no more than about 50 centimeters. This is about as short as the leads can be and still enable the electrodes to be properly positioned. Thus, as a practical matter, it may be extremely difficult to devise means for coupling an electric field into a human patient where the frequency used is much higher than about 15 MHz.

As previously mentioned, the lower limit on the frequency utilized is about 2 MHz. Below this frequency, any significant amount of bone in the field may cause problems in providing adequate coupling of the field to the tissue. Moreover, with lower frequencies, the coils in the apparatus and in the handles of the paddles must be correspondingly larger and at frequencies lower than about 2 MHz may become so bulky as to be impractical. Naturally, the frequency used should also be above that of any neuromuscular reaction. A lower limit of about 2 MHz assures this. Experiments on simulated tissue at frequencies extending over the range of about 2 MHz to about 15 MHz indicate very little variation in heating efficiency between different frequencies in the range.

In applying the electric field to tissue in accordance with the invention, it is important to prevent excessive damage to the healthy tissue while at the same time maintaining a high enough temperature in the tumor over a sufficient period of time so as to kill the tumor. The fact that the maintenance of a high enough temperature over a sufficiently long period of time will kill many types of tumors is, as previously mentioned, documented in the prior art. Applicant's invention has provided a method and means for accomplishing this through the use of an electric field wherein it is possible to closely control the amount of energy being applied to the tissue and thus closely regulate the temperatures in accordance with the desired treatment. The use of frequencies in the range previously specified, together with the avoidance of high loss factors, make it possible to employ electric fields in such a way as to destroy tumors without significant damage to the surrounding healthy tissue. Using a heating rate of about 20 minutes for a 5° F. rise in the healthy tissue surrounding the tumor, the temperature inside a tumor has been observed to increase from two to three times as much as the temperature in the surrounding healthy tissue.

Figure 2:
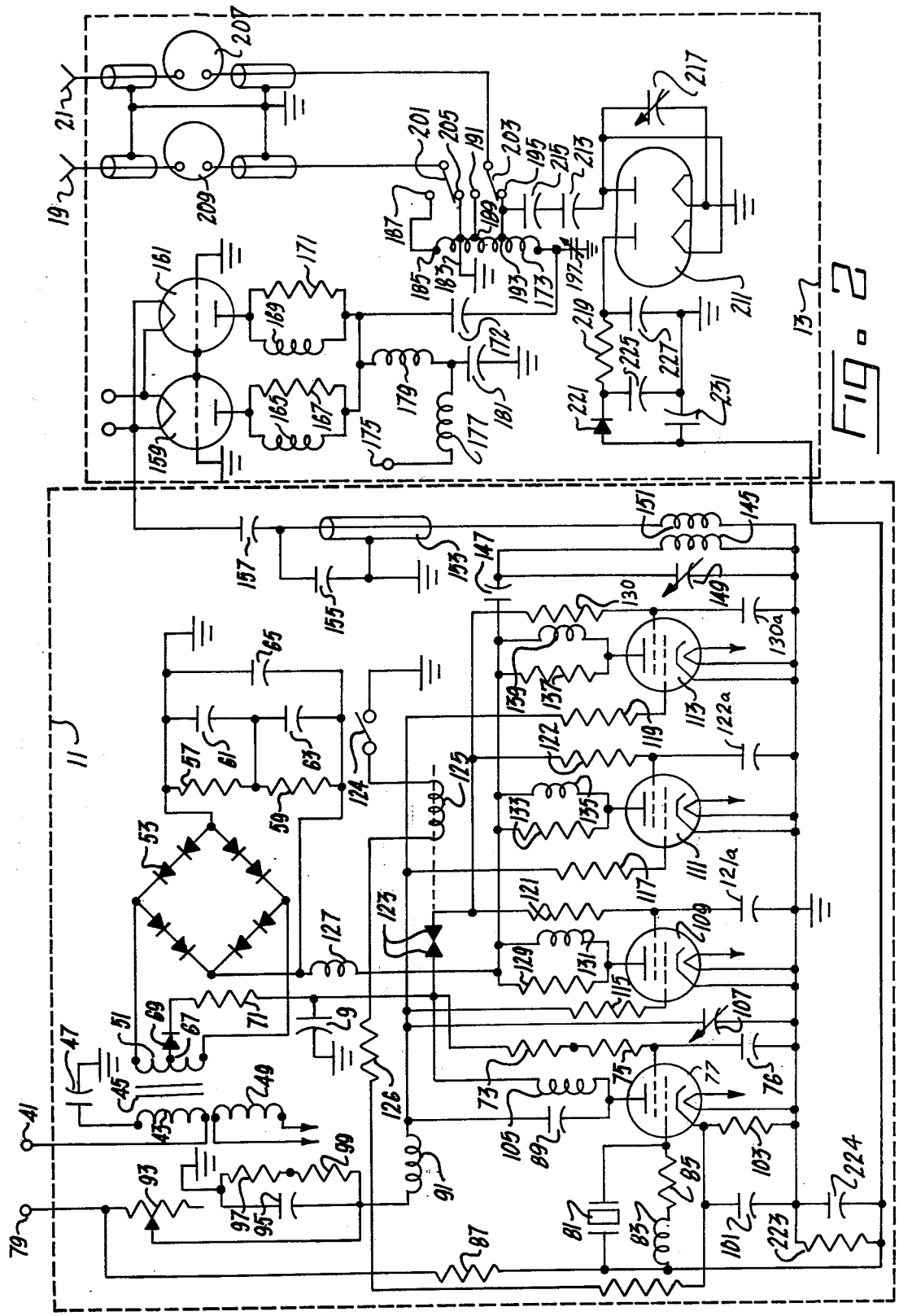
FIG. 2 is a circuit diagram illustrating one form of a portion of the apparatus of the invention.

Referring now more particularly to FIG. 2, there is illustrated a schematic diagram of circuitry for use as the RF oscillator 11 and the amplifier 13. A 60 c.p.s. 117 V. or other suitable a-c supply is applied to the primary winding 43 of a power transformer 45, the primary being bypassed to ground through a capacitor 47. Included in the power transformer 45 is a secondary winding 49 to which are connected the filaments of the vacuum tubes described below. The secondary winding 51 of the power transformer 45 is connected across a diode bridge rectifier 53. Completing the diode circuitry are a pair of resistors 57 and 59 connected across opposite corners of the bridge, capacitors 61 and 63 in parallel therewith, respectively, and a capacitor 65 connected in parallel with the capacitors 61 and 63. The junction between the capacitors 57 and 59 is connected to the junction between the capacitors 61 and 63.

A center tap 67 on the secondary winding 51 is connected through a diode 69, a resistor 71, a filter capacitor 9 to ground, and resistors 73 and 75 to the screen of a tetrode 77. The resistors 73 and 75 are connected to ground through a capacitor 76. The tetrode 77 functions as the RF oscillator element in the oscillator 11, having its grid connected to a bias source terminal 79 through a resistor 87 and a tank circuit. The tank circuit includes a quartz crystal 81, a coil 83 and a resistor 85 in series with the coil 83. The plate of the tetrode 77 is connected to the choke 105 and through a plate capacitor 89, to the resistors 115, 117 and 119, in the control grids of tetrodes 109, 111 and 113. Coupled to the low side of the choke 91 is a capacitor 95 and a pair of series resistors 97 and 99 connected in parallel with the capacitor to ground. The cathode of the tetrode 77 is grounded through a capacitor 101 and parallel resistor 103. The bias source is from 79 through a variable resistor 93.

The RF output of the tetrode 77 at the plate thereof is coupled through a tuned circuit including a coil 105 and a variable capacitor or tuning capacitor 107 to a parallel amplifier including three tetrodes 109, 111 and 113. RF drive and grid bias for the three amplifier tubes is provided through resistors 115, 117 and 119, respectively. Screen grid bias is provided by resistors 121, 122 and 130, and by capacitors 121a, 122a, and 130a. Plate voltage for the tetrode 109 is supplied through a choke coil 127 and the parallel combination of a resistor 129 and a coil 131 from the diode bridge rectifier 53. The parallel combination of the resistor 133 and coil 135 supplies the plate voltage for the tube 111 and the parallel combination of the resistor 137 and the coil 139 provides the plate voltage for the tube 113. The tubes 109, 111 and 113, therefore, operate in parallel to amplify the output of the RF oscillations of the tube 77.

The contacts 123 of a relay 125 are interposed between the resistor 121 and the plate of the tetrode 77.

One side of the relay 125 is connected to ground through a normally closed reset switch 124. The other side of the relay 125 is connected through a resistor 126 to the cathode of the tube 77.

The amplified oscillations of the RF oscillator-amplifier 11 are developed across an output transformer having a primary winding 145 in series with the capacitor 147 and having a variable capacitor 149 connected thereacross. The smaller secondary winding 151 of the output transformer passes its signals through a shielded coaxial cable 153 having a tuning capacitor 155, through a coupling capacitor 157 to the amplifier 13.

The amplifier 13 includes a pair of parallel triodes 159 and 161. The grids of the triodes are grounded and the input from the RF oscillator 11 is coupled to the cathodes of the triodes 159 and 161 through the coupling capacitor 157. The plate output circuit of the triode 159 includes a parallel combination of a coil 165 and resistor 167. The plate output circuit of the triode 161 includes the parallel combination of a coil 169 and a resistor 171. The d-c voltage is provided from a high voltage terminal 175 through a choke coil 177 and a further choke coil 179. A capacitor 181 bypasses the coils 177 and 179 to ground.

A capacitor 172 couples the plate RF output of the parallel triode amplifiers 159 and 161 through an autotransformer 173. The autotransformer 173 includes a tap 183 which is grounded. A further winding on the transformer 173 has a tap 185 which is connected to a terminal 187. A tap 189 toward the higher voltage end of the transformer 173 is connected to a terminal 191. A further tap 193 closer to the input end of the transformer 173 than the tap 189 is connected to a terminal 195. The transformer 173 is tuned by a variable capacitor 197.

The output of the amplifier 13 is derived through a relay with one contact 201 for a left channel and a second contact 203 for a right channel. The relay contact 201 in the illustrated position connects to a grounded terminal 205 and is for the purpose of operating the apparatus in the mode illustrated in FIG. 3. In this condition, the relay contact 203 connects with the terminal 195, thereby supplying a radio frequency signal between the tap 193 and ground. This signal is applied through a meter 207 to the output socket or terminal 21. In the event two electrodes or paddles are used, as in FIG. 1, the relay contacts 201 and 203 are moved to the terminals 187 and 191, respectively, when the output from the terminal 187 is applied through a meter 209 to the left socket or output terminal 19.

For the purpose of stabilization and control, a d-c coupled servo loop or feedback loop is provided. The servo loop includes a voltage doubler diode 211 in which the left-hand one of the plates is coupled through a pair of capacitors 213 and 215 to the terminal 195. A variable capacitor 217 is connected between that plate and its corresponding grounded cathode for adjusting the power level at which the apparatus is being operated. The right-hand plate of the diode 211 is connected through a resistor 219 and a diode 221 to the coil 83 of the grid return of the tetrode oscillator tube 77 in the oscillator-amplifier 11. The signal thus applied is developed across the parallel combination of the resistor 223 and capacitor 224 in the oscillator 11. The plate signal is developed across a capacitor 227 connecting the plate side of the resistor 219 to ground. A capacitor 225 connects the opposite side of the resistor 219 to ground. A capacitor 231 is connected to ground from the opposite side of the diode 221 from the resistor 219. The right-hand cathode of the doubler diode 211 is connected to the left-hand plate such that the dual diodes of the tube 211 are coupled in series. Adjustment of the capacitor 217 sets the power level at which the apparatus operates by adjusting the grid voltage on the tube 77, and is capable of an approximate fifteen-fold variation.

The above discussed circuit configuration permits the apparatus to be operated by a single control adjusting the capacitor 217. There is no need for the operator of the apparatus to do any tuning of the circuit. This is because the direct current inverse feedback provided by the circuit 17 stabilizes the current at any given control setting even if the resistive and/or capacitive loads vary. Thus, for example, if the apparatus is utilized to treat a lung tumor, and if the electric field passes through the lung, the current is stabilized at the control setting even though the air path in the lung through which the field passes varies in length with the breathing of the patient.

In the event that the doubler diode 211 fails, power output may tend to increase dangerously. To prevent this, the relay 125 is set to open the contacts 123 when the cathode current of the tube 77 increases beyond a preselected level. When the relay switch or contacts 123 open, screen bias to the tubes 109, 111 and 113 is removed, cutting off the RF power.

For the purpose of illustrating the apparatus of the invention, the following examples are given. It is not intended, however, that the invention be limited in any way to the specific parameters or procedures set forth in the examples.

EXAMPLE 1.

To demonstrate the uniformity of heating and absence of skin eddy currents, apparatus constructed in accordance with the invention was utilized to pass an electric field through a bag containing three liters of salt-agar jelly. Using a radio frequency of 13.56 MHz, power levels of 300 to 400 watts were used. Temperatures were measured adjacent to opposite sides of the jelly and in the center of the jelly using highly accurate centigrade thermometers. With an increase in temperature of over 30° C. the maximum observed difference in temperature readings was 6.5° C. Where conditions and the configuration of the apparatus were carefully controlled, temperatures were maintained within 2° C. and in most cases substantially less. More importantly, however, there was no indication of a tendency for greater heating near the surface than in the center demonstrating that the degree of heating was uniform regardless of depth and was not affected by the presence of eddy currents in the skin as is the case typically in connection with electromagnetic fields.

EXAMPLE 2.

A "terminal" patient having a malignant tumor in the right lung complained of constant pain before treatment and pain in the right shoulder when the right arm was moved. The patient was treated using apparatus constructed in accordance with the invention using a single electrode and a grounded table. The following indicates the procedure:

| Time After Starting Treatment | Skin Surface Temp. at Electrode ° C. | Approximate Power Output in Watts |
| --- | --- | --- |
| 0 min. | 35.65 | 50 |
| 1 min. | 37.10 | 50 |

| Time After<br>Starting Treatment | Skin Surface Temp.<br>at Electrode ° C. | Approximate<br>Power Output<br>in Watts |
|---|---|---|
| 2 min. | 37.1 | 60 |
| 3 min. | 37.1 | 60 |
| 4 min. | 37.35 | 60 |
| 6 min. | 37.5 | 60 |
| 8 min. | 38.35 | 60 |
| 10 min. | Shut off apparatus to further sedate patient. | |
| restart | 37.7 | 50 |
| 2 min. | 38.6 | 50 |
| 3 min. | 38.7 | 50 |
| 4 min. | 38.7 | 50 |
| 6 min. | 38.35 | 50 |
| 8 min. | 38.2 | 45 |
| 10 min. | 38.2 | |

After treatment, the patient indicated that he felt no pain and had increased mobility in his right arm. Several weeks after treatment, the patient was discharged from the hospital.

EXAMPLE 3.

A patient having a malignant tumor in the left lung considered terminal was treated using apparatus constructed in accordance with the invention using two electrodes as follows:

| Time After<br>Starting Treatment | Skin Surface Temp.<br>at Chest Electrode ° C. | Approximate<br>Power Output<br>in Watts |
|---|---|---|
| 0 min. | 37.7 | 50 |
| 2 min. | 37.8 | 50 |
| 5 min. | 38.2 | 50 |
| 7 min. | 38.6 | 60 |
| 9 min. | 39.0 | 60 |
| 11 min. | 39.0 | 60 |
| 13 min. | 39.0 | 60 |
| 14 min. | 39.1 | 60 |
| 17 min. | 39.1 | 60 |
| 19 min. | 39.2 | 70 |
| 21 min. | 39.3 | 70 |

Several weeks after treatment, the patient was discharged from the hospital.

EXAMPLE 4.

A male patient having a hard malignant tumor about the size of a baseball on the front of his throat was treated using apparatus constructed in accordance with the invention. For a long period before treatment, the patient had difficulty in breathing such that it was necessary to provide him constantly with oxygen, and he was unable to speak. A single electrode was used and the table upon which the patient was lying was grounded. Copper wool was shaped to conform to the approximately spherical external shape of the tumor. The treatment was carried out for approximately 45 minutes utilizing a power of approximately 200 watts. The oral temperature was checked repeatedly during treatment and it did not exceed 104° F. (40° C.).

Approximately 6 hours after cessation of treatment, the patient was examined and it was noted that the tumor had decreased in size and was soft. Less than 24 hours later, it was no longer necessary to provide the patient with oxygen and the patient was beginning to whisper. The tumor was further reduced in size. One week after treatment, the tumor had reduced to a size of "about a silver half-dollar". Biopsies performed on the material taken from the area of the tumor before the treatment showed the tumor to be malignant while a biopsy taken one week after treatment showed nothing but dead tissue and no malignant cells.

It may be seen, therefore, that the invention provides an effective apparatus for treating tumors by causing the tumors to increase in temperature substantially above that of the surrounding healthy tissue. It is believed that such procedure causes the tumor to be destroyed in many cases, and that the resulting rise in temperature is due to the substantially reduced circulation present in malignant tumors. The invention is also capable of heating other types of tissue which have a substantially lower circulation rate than surrounding tissue to temperatures higher than the surrounding tissue.

Various modifications of the invention in addition to those shown and described herein will become apparent to those skilled in the art from the foregoing description and accompanying drawings. Such modifications are intended to fall within the scope of the appended claims.

What is claimed is:

1. Apparatus for treating tumors in humans and animals, comprising, radio frequency oscillator means for producing a radio frequency output signal, amplifier means coupled to the output of said radio frequency oscillator means for producing an amplified radio frequency output signal, electrode means coupled to said amplifier means, said electrode means including at least one capacitive electrode having a configuration adapted to pass an electric field through both the tumor and the surrounding tissue, and means for controlling the power of said amplifier means to avoid heating the surrounding tissue beyond a preselected temperature level while allowing the tumor to heat beyond the preselected temperature level, said controlling means including direct current inverse feedback means connected from said amplifier means to said oscillator means for stabilizing output current, said feedback means including means for adjusting the voltage of the direct current feedback to adjust the power level of the output of said amplifier means.

2. Apparatus according to claim 1 including coaxial conductor means connecting said amplifier means to said electrode means, said coaxial conductor means having a total length of less than about one-twentieth of the wavelength of the radio frequency output signal.

3. Apparatus according to claim 1 wherein said capacitive electrode is insulated with a low-loss dielectric material.

4. Apparatus according to claim 1 wherein said electrode means comprise two capacitive plates.

5. Apparatus according to claim 1 including inductance means in series with said electrode means between said electrode means and said amplifier means and having an inductive reactance substantially equal to the capacitive reactance of said electrode means.

6. Apparatus according to claim 1 wherein said oscillator means and said amplifier means are constructed to provide an output signal at a frequency of between about 2 MHz and about 40 MHz.

7. Apparatus according to claim 1 including coaxial cable means connecting said amplifier means to said electrode means, said coaxial cable means having a total length of less than about one-twentieth of the wavelength at the frequency of the output signal of said amplifier means.

8. Apparatus according to claim 7 wherein said electrode means includes two capacitive electrodes and said coaxial cable means comprises two coaxial cables connecting respective ones of said electrodes to the amplifier means, each said coaxial cable includes a conductive sheath, said apparatus including jumper means connecting said sheaths of said coaxial cables and providing a return path for ground currents.

9. Apparatus according to claim 1 including cut-off circuit means responsive to an output power level of said amplifier means exceeding a predetermined amount to cut off power to said apparatus.

10. Apparatus for treating tumors in humans and animals comprising, radio frequency oscillator means for producing a radio frequency output signal, amplifier means coupled to the output of said radio frequency oscillator means for producing an amplified radio frequency output signal, said oscillator means and said amplifier means being constructed to provide an output signal at a frequency of between about 2 MHz and about 40 MHz, electrode means coupled to said amplifier means, said electrode means including at least one plate having a configuration adapted to pass an electric field through both the tumor and the surrounding tissue, coaxial cable means connecting said amplifier means to said electrode means, said coaxial cable means having a total length of less than about 1/20th of the wavelength at the frequency of the output signal of said amplifier means, and means for controlling the power of said amplifier means to avoid heating the surrounding tissue beyond a preselected temperature level while allowing the tumor to heat beyond the preselected temperature level, said controlling means comprising inverse direct current feedback means connected from said amplifier means to said oscillator means for stabilizing output current, said feedback means including means for adjusting the voltage of the direct current feedback to adjust the power level of the output of said amplifier means.

* * * * *